United States Patent
Gregersen (10) Patent No.: US 7,479,120 B2
(45) Date of Patent: Jan. 20, 2009

(54) METHOD AND APPARATUS FOR INVESTIGATING FORCE-DEFORMATION PROPERTIES IN MUSCLES IN WALLS OF BODILY HOLLOW SYSTEMS

(76) Inventor: Hans Gregersen, Ågårdvej 1, Hornslet DK-8543 (DK)

(*) Notice: Subject to any disclaimer, the term of this patent is extended or adjusted under 35 U.S.C. 154(b) by 39 days.

(21) Appl. No.: 10/505,223

(22) PCT Filed: Feb. 21, 2003

(86) PCT No.: PCT/DK03/00119

§ 371 (c)(1),
(2), (4) Date: Feb. 1, 2005

(87) PCT Pub. No.: WO03/070091

PCT Pub. Date: Aug. 28, 2003

(65) Prior Publication Data

US 2005/0124920 A1   Jun. 9, 2005

(30) Foreign Application Priority Data

Feb. 22, 2002 (DK) .............................. 2002 00280

(51) Int. Cl.
*A61B 5/103* (2006.01)
*A61B 5/117* (2006.01)

(52) U.S. Cl. .................................................. 600/587
(58) Field of Classification Search ................ 600/587, 600/585, 593

See application file for complete search history.

(56) References Cited

U.S. PATENT DOCUMENTS

| 2,979,055 | A | * | 4/1961 | De Beer et al. ............. 604/507 |
| 4,566,465 | A | * | 1/1986 | Arhan et al. ................ 600/591 |
| 4,600,015 | A | * | 7/1986 | Evans et al. ................ 600/593 |
| 4,809,710 | A | * | 3/1989 | Williamson ................ 600/561 |
| 5,316,016 | A | * | 5/1994 | Adams et al. ............... 600/587 |
| 5,617,876 | A | | 4/1997 | Van Duyl |
| 5,623,939 | A | * | 4/1997 | Garfield ...................... 600/546 |
| 5,752,522 | A | * | 5/1998 | Murphy ...................... 600/587 |

(Continued)

FOREIGN PATENT DOCUMENTS

DK   WO 03/020124   *  3/2003

(Continued)

OTHER PUBLICATIONS

Rao et al. "Unexplained Chest Pain: The Hyper sensitive, Hyperreactive, and Poorly Compliant Esophagus." Ann. Intern. Med. 124: 950-958, 1996.*

(Continued)

*Primary Examiner*—Max Hindenburg
*Assistant Examiner*—Rene Towa
(74) *Attorney, Agent, or Firm*—Stephen A. Bent; Foley & Lardner LLP (57) ABSTRACT

The invention relates to a method for investigating force-deformation properties in muscles in walls of bodily hollow systems. The invention also relates to an apparatus for performing such investigating force-deformation properties in muscles in walls of bodily hollow systems and the use of such apparatus. By the method and the apparatus it is possible from measurements made deriving data on force-deformation relationship in the walls of the hollow system in order to obtain knowledge on active and passive tissue properties.

24 Claims, 4 Drawing Sheets

U.S. PATENT DOCUMENTS

| | | | | |
|---|---|---|---|---|
| 5,865,801 A | * | 2/1999 | Houser | 604/103.07 |
| 5,924,984 A | * | 7/1999 | Rao | 600/373 |
| 6,203,508 B1 | | 3/2001 | Ren et al. | |
| 6,210,343 B1 | * | 4/2001 | Kanakaris et al. | 600/504 |
| 6,468,232 B1 | * | 10/2002 | Ashton-Miller et al. | 600/591 |
| 6,773,452 B2 | * | 8/2004 | Shaker | 600/587 |
| 2006/0030792 A1 | * | 2/2006 | Annest et al. | 600/587 |
| 2006/0057188 A1 | * | 3/2006 | Gaetani | 424/439 |

FOREIGN PATENT DOCUMENTS

| | | |
|---|---|---|
| EP | 0 489 516 A | 6/1992 |

OTHER PUBLICATIONS

International Search Report.

* cited by examiner

METHOD AND APPARATUS FOR INVESTIGATING FORCE-DEFORMATION PROPERTIES IN MUSCLES IN WALLS OF BODILY HOLLOW SYSTEMS

FIELD OF THE INVENTION

The present invention relates to a method for investigating force-deformation properties in muscles in walls of bodily hollow systems. The invention also relates to an apparatus for performing such investigating force-deformation properties in muscles in walls of bodily hollow systems and the use of such apparatus.

BACKGROUND OF THE INVENTION

The function of visceral organs like the gastrointestinal tract, the urinary tract and the blood vessels is to a large degree mechanical. The following introduction refers mainly to the gastrointestinal tract but the invention relates to similar applications in other hollow organs.

In the gastrointestinal tract, contents received from the stomach are propelled further down the intestine and mixed with secreted fluids to digest and absorb the food constituents. The biomechanical properties of the small intestine in vivo are largely unknown, despite the fact that the distensibility is important for normal function, and altered mechanical properties are associated with gastrointestinal (GI) diseases. Data in the literature pertaining to the mechanical aspects of GI function are concerned with the contraction patterns, the length-tension relationship in circular and longitudinal tissue strips in vitro, flow patterns, the compliance and the tension-strain relationship. The methods traditionally used for clinical or basic investigations of the small intestine are endoscopy, manometry and radiographic examinations. Although these methods provide important data on the motor function, little attention has been paid to biomechanical parameters such as wall tension and strain and the relation between biomechanical properties and sensation. During the past two decades, impedance planimetry was used in gastroenterology to determine wall tension and strain in animal experiments and human studies. Impedance planimetry provides a measure of balloon cross-sectional area and is therefore a better basis than volume measurements for determination of mechanical parameters such as tension and strain in cylindrical organs.

GI symptoms are often associated with disturbances in motility and sensory function in the GI tract. Several studies attempted to investigate these properties by means of balloon distension. {Schultz & Corkeron 1994 31/id} Unfortunately, the primary mechanism for symptoms elicited by GI distension remains unclear. It is well known that distension of the gastrointestinal tract elicits reflex-mediated inhibition and stimulation of motility via intrinsic or extrinsic neural circuits and induces visceral perception such as pain. Previous studies demonstrated that mechanoreceptors located in the intestinal wall play an important role in the stimulus-response function. It is, however, a common mistake to believe that mechanoreceptors are sensitive to variation in pressure or volume. A large variation in the peristaltic reflex and perception has been found in various studies, suggesting that pressure is not the direct stimulus. Instead, the receptors are stimulated by mechanical forces and deformations acting in the intestinal wall due to changes in the transmural pressure. Thus, the mechanical distension stimulus and the biomechanical tissue properties must be taken into account in studies of the sensory-motor function in the intestine.

It is well known that the passive elastic behaviour of biological tissues is exponential. The exponential behaviour protects the organs including the intestine against overdistension and damage at high luminal pressure loads and allows the intestine to distend easily to facilitate flow in the physiological pressure range. In arteries, it has been demonstrated. that collagen bears circumferential loads at high stress levels. Since gastrointestinal tissue is rich in collagen, it is likely that collagen is a major determinant of the curve shape. The passive elastic behaviour (tension-strain relation) of duodenum in vivo is exponential and hence can play a role in protecting tissue against high stress. At high loads the mechanical behaviour is contributed mainly by the passive tension curve, whereas at low stress levels, that is in the physiological range, the active tension curve also affects the tissue behaviour. Thus, the distensibility in vivo depends not only on the passive properties but also on the physiological state of smooth muscle.

Mechanical properties have been studied in vitro in muscle tissue strips from various organs. The strips are mounted in a small organ bath between hooks so the strip can be elongated in a controlled way and the resultant force measured. This has made possible studies of isometric and isotonic muscle length-tension diagrams in vitro. Usually the tissue has been studied when influenced by drugs such as muscle relaxants and muscle stimulants, in order to study active and passive tissue properties. The passive curve is normally described as exponential whereas the active curve is bell-shaped, i.e. with a maximum. The maximum active tension is presumably reached at a level of optimum overlap between the sliding filaments in the intestinal muscle cells. in vivo no such method exists. Manometry is used to record the contraction patterns but it gives no information about the passive mechanical properties but only indirect data on the force of contraction. Balloon distension techniques, which record balloon pressure and balloon dimensions such as volume and cross-sectional area, can provide a mechanical stimulus to the wall. But in the way these techniques have been used, data on the smooth muscle force have been sparse and control of passive conditions have been insufficient.

SUMMARY OF THE INVENTION

The object of the present invention, according to a first aspect, is to provide a method and an apparatus capable of applying stimuli to the bodily hollow system and simultaneously measuring physical properties of the apparatus applying the stimuli. A further object of the invention, according to a second aspect, is to provide a method and an apparatus for measuring force-deformation data from humans or animals, where the measuring takes place simultaneously with applying stimuli or in alternative to applying stimuli.

The invention is designed to measure active and passive wall mechanical reactions towards stimulation by introducing from an exteriorly accessible opening of a bodily hollow system a catheter into the hollow system, said catheter being provided with an inflatable balloon situated between a proximal end and a distal end of the catheter, and inflating the balloon until the balloon abuts an inner wall of the hollow system, under the conditions where the muscle cells are passive, maximally contracted or some intermediate state obtained during use of pharmacological substances intended for activation or relaxation of muscles or for the influence of nerve functions.

The invention comprises a further development of balloon distension methods by providing force-deformation diagrams such as tension-strain measures in vivo before and during administration of muscle relaxant or muscle stimulating drugs. Hereby, active and passive properties can be studied in vivo or in whole segments in vitro and can be related to other physiological responses such as to pain elicited by the mechanical stimulation. Development of balloon distension protocols is useful in order to correlate biomechanics, motor control and visceral non-pain and pain perception in the visceral organs, in particular in the gastrointestinal tract in vivo and in vitro. The distension can be used to derive isometric and isotonic length-tension data in vivo with subsequent evaluation of the circumferential wall tension, strain, reflex-induced motor activity and sensory intensity. In relation to the wall tension, it is the active, passive and total forces inducing tension and stress, which is derived. This length-tension test provides data on the passive nature of the tissue, on the maximum force generated by the smooth muscle, and the strain corresponding to the maximum force.

The object according to the first aspect of the invention is obtained by a method comprising the steps of:

inflating the balloon until the balloon abuts an inner wall of the hollow system in order for the balloon and the catheter to be fixed in relation to the hollow system, introducing a mechanical stimulation into the hollow system by inflating the balloon under a number of conditions of the hollow system such as pharmacological intervention, measuring a change of a physical property of the balloon during inflation of the balloon, said physical property being a dimensional state of the balloon itself, alternatively said physical property being correlated to a force induced to the balloon, alternatively said physical property being a mutual state between the balloon and the wall of the hollow system, and- from the measurement deriving data on force-deformation relationship in the walls of the hollow system in order to obtain knowledge on active and passive tissue properties.

If the measurements are performed in vivo, the method comprises the initial step of introducing from an exteriorly accessible opening of a bodily hollow system a catheter into the hollow system, said catheter being provided with an inflatable balloon situated between a proximal end and a distal end of the catheter, It is important to notice that by the denomination "balloon" is meant only a bag capable of being inflated. The inflation need not result in a dilation of the material of the balloon. Thus, perhaps the balloon is made of a material, which subsequent to inflation is not subjected to any stretching, but merely has an increased volume due to the inflation. Accordingly, in the whole application, apart from in the test results in the last part of the specification, the denomination "balloon" will be used, because this is the commonly used denomination, although the balloon maybe as a bag, i.e. no dilation of the bag.

An apparatus for performing the method according to the first aspect comprises a catheter that is provided with an inflatable balloon situated between a proximal end and a distal end of the catheter, and the apparatus comprises means for passing an inflating fluid, preferably a liquid, from the proximal end to the balloon, and furthermore comprises means for recording and controlling the temperature in the balloon of the catheter.

The object according to the second aspect of the invention is obtained by a method comprising the steps of:

inflating the balloon as a stepwise distension or a ramp distension with controlled distension rates until the balloon abuts the inner wall of the hollow system in order for the balloon and the catheter to be fixed longitudinally in relation to the hollow system and for mechanical stimulation of the system, measuring a change of a physical state of the hollow system during inflation of the balloon, said physical state of the hollow-system being correlated to a corresponding physical property of the balloon, alternatively said physical state of the hollow system being correlated to a mutual state between the balloon and the wall of the hollow system, and from the measurements deriving force-deformation diagrams such as length-tension diagrams, pressure-volume diagrams, tension-strain diagrams, and stress-strain diagrams under various conditions such as during administration of drugs in animals or persons with diseases.

In case the measurements are made in vivo, preferably the balloon is introduced from an exteriorly accessible opening of a bodily hollow system a catheter into the hollow system, said catheter being provided with an inflatable balloon situated between a proximal end and a distal end of the catheter, An apparatus for performing the method according to the second aspect comprises a catheter that is provided with an inflatable balloon situated between a proximal end and a distal end of the catheter, and the apparatus comprises means for passing an inflating fluid, preferably a liquid, from the proximal end to the balloon, and where the apparatus is provided with means for measuring at least one of the following physical properties of the balloon: the volume of the balloon, the cross-sectional area of the balloon seen in a direction parallel to a longitudinal extension of the bodily hollow system, when the apparatus is introduced into the body, the diameter of the balloon in a plane perpendicular to a longitudinal extension of the bodily hollow system, when the apparatus is introduced into the body, the tension of the balloon, the strain of the balloon, the pressure of a fluid inside the balloon, and the temperature of a fluid inside the balloon, the apparatus intended for measuring a physical reaction of a person or an animal, when a bodily hollow system of the person or the animal is being subjected to a number of artificially applied stimuli.

BRIEF DESCRIPTION OF THE DRAWINGS

The invention will now be described in detail with reference to the drawing, where.

DETAILED DESCRIPTION OF THE INVENTION

Figure 1:
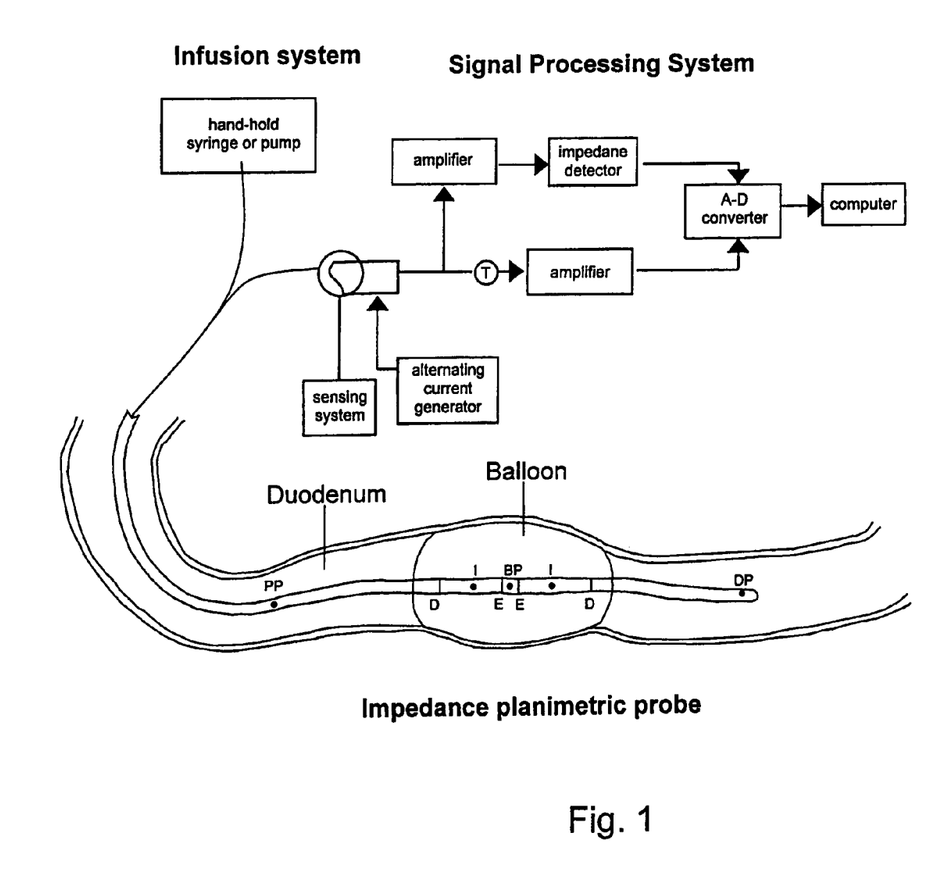
FIG. 1 is a sketch showing an apparatus according to the invention being introduced into the small intestine of a patient for physical stimulation and/or measuring properties. The sketch demonstrated an embodiment with impedance planimetric recording of cross-sectional area of the balloon along with pressure recordings.

FIG. 1 shows how an apparatus for providing stimuli and/or for measuring certain properties in a bodily hollow system may be utilised in the small intestine of a patient. The apparatus consists of a catheter, alternatively denoted a probe, having a proximal end and a distal end. The distal end is introduced into a readily accessible opening from the outside, i.e. the mouth or, as shown, the nose and further down into the small intestine. Nearby the distal end, the catheter is provided with a balloon, also called a bag, which is inflated so that an outer surface of the balloon is abutting the inner surface of the wall of the hollow system, i.e. of the small intestine. The inflation takes place only after the catheter has been introduced into the small intestine. By inflating the balloon, the balloon and thus the catheter is fixed in relation to the small intestine so that the catheter, in the situation shown, cannot be displaced longitudinally along the length of the small intestine.

Preferably, but not necessarily, the catheter is fixed at the proximal end as well, i.e. is fixed to the nose or any other outer surface or organ. In the situation shown, where the catheter is introduced through the nose, fixation of the proximal end may take place in any suitable manner, perhaps by a clamp being clamped to the wing of the nose, to the nasal bone or to the bridge of the nose. Once introduced into the bodily hollow system, the apparatus may be used for stimulation of the hollow system of a person or an animal by mechanical stimulus. Alternatively, or in addition, the apparatus may be used for measuring a physical reaction of a person or an animal, when the bodily hollow system of the person or the animal is being subjected to a number of artificially applied stimuli of the above-mentioned type.

The balloon of the catheter is preferably made from polyestherurethane being a material readily extendable, being non-harmful to the human or animal body and having distinct physical properties such as elasticity, modulus of strain etc. The thickness of the material, which the balloon is made of, is perhaps between 30 μm and 50 μm. However, any other well-suited material may be used as long as it fulfils the need for enlargement, non-permeability of the fluid inflating of the balloon, perhaps non-permeability of electrical currents, and security towards not being harmful to the body. Thus, polypropylene (PP) or polyethylene (PE) may alternatively be used. Even other materials may be used referring to the fact that the denomination "balloon" need not imply that the material, which the balloon is made of, is dilated, when the balloon, or the bag which it may also be called, is inflated. Thus, materials having much less elasticity than the above-mentioned materials may be used, perhaps materials which, when inflated, does not show any noticeably elastic deformation. Also the thickness of the material, which the balloon is made of, may be thicker than the dimensions mentioned above, thus perhaps also resulting in that the material, when inflated, does not show any noticeably elastic deformation.

The size of the balloon, when inflated, differs depending on which bodily hollow system the apparatus is used in and depending on which part of the system in question, that the apparatus is used in. As example, for use in the small intestine, the balloon normally has a size when being inflated of up to 40 mm in diameter seen in a plane perpendicular to the longitudinal direction of the small intestine. However, abnormalities of the small intestine such as dilatation may necessitate a balloon having an increased diameter when inflated. Also, other hollow systems have either smaller or larger cross-sectional areas than the small intestines. Thus, the cardiovascular system have much smaller cross-sectional areas, whereas the small intestine and even the large intestine and the rectum normally have larger diameters than the small intestine, perhaps necessitating a balloon having up to 80 mm in diameter when inflated.

In the situation shown, the apparatus shown is a longitudinal catheter being introduced into the small intestine of a human being. However, the apparatus may be used on animals as well. Furthermore, the apparatus may be used in any hollow system of the body of the person or the animal, either in vivo or in vitro, non-limiting examples of such hollow systems being: the digestive system including the stomach, preferably the gastrointestinal tract, a part of the urogenital system including the urinary bladder, or part of the cardiovascular system including the heart.

Figure 2:
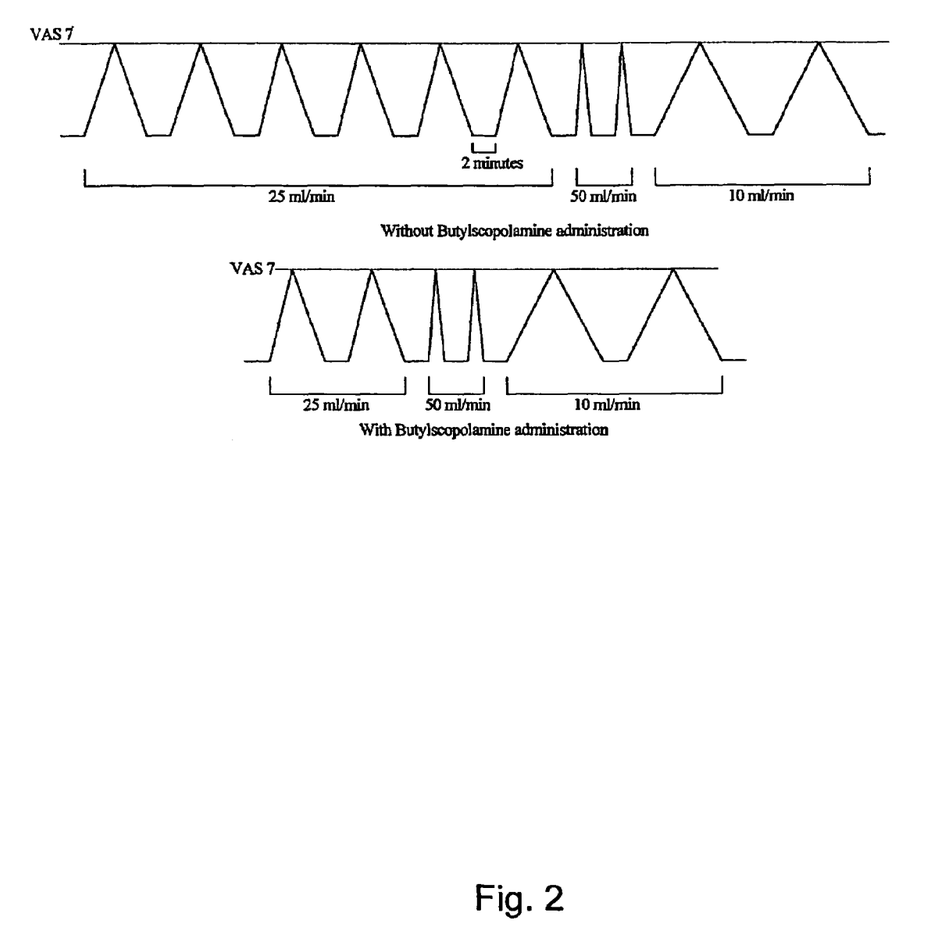
FIG. 2 is a sketch of a ramp distension protocol where the tissue is preconditioned and thereafter the tissue is distended at various distension rates and without or with infusion of a muscle relaxant.

FIG. 2 shows an example of distension protocols. In this case the balloon can be inflated and deflated in a controlled manner either manually but preferable with a pump that can be used manually or controlled by a PC. As illustrated in the figure the infusion rate can be varied and the distension repeated during different drug treatments. The distension is done by means of a fluid, preferably a liquid, and more preferred salt water introduced to the balloon through a canal (see FIG. 1) provided in the catheter. The fluid is pumped to the balloon from an exterior reservoir such a sterile bag containing the fluid, the pumping being provided by, as example, a pump with rollers exerting a pumping action on a hose, and the fluid is pumped from the reservoir to the proximal end of the catheter. The pressure of the fluid is monitored, possibly by a pressure gauge inside the balloon. Alternatively to measuring the pressure, the volume of the fluid being pumped to the balloon may be monitored, either when being pumped to the balloon or after having been pumped to the balloon. The inflation of the balloon constitutes a mechanical stimulus of the hollow system.

Figure 3:
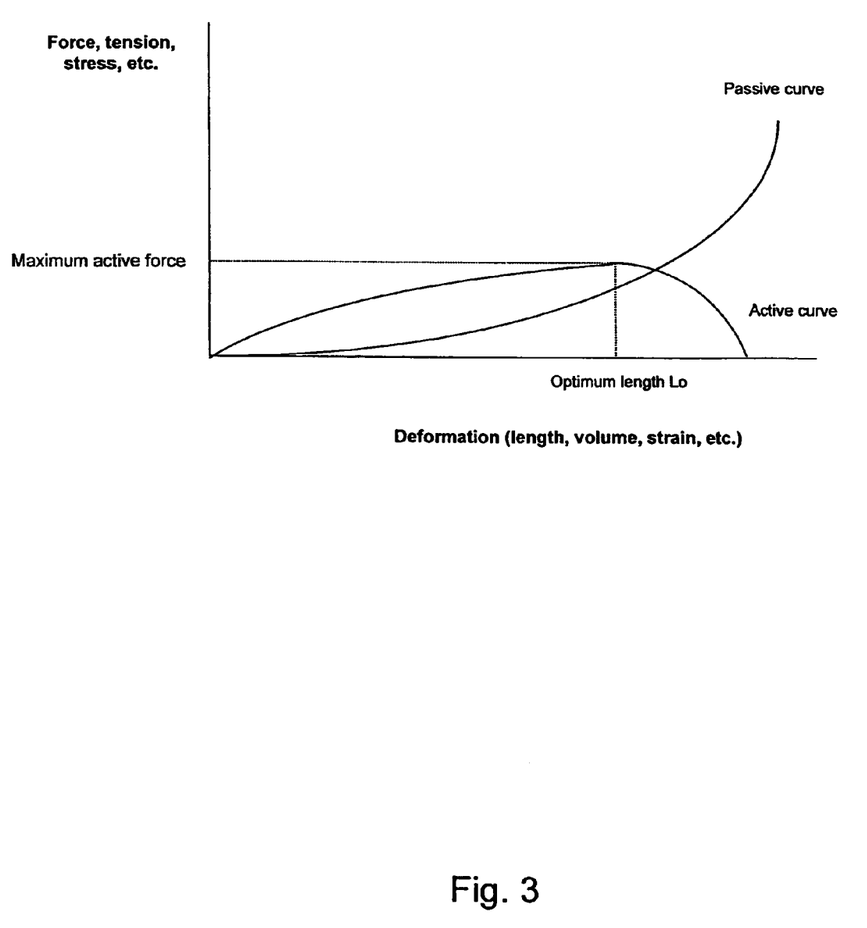
FIG. 3 is a sketch of a classical length-tension diagram for uniaxial stretching of muscle tissue.

FIG. 3 illustrates a classical length-tension diagram as can be determined for muscle tissues in vitro and which is made possible by the invention in vivo or in vitro in hollow organs. The passive curve is exponential like whereas the active curve is bell-shaped and characterised by a maximum force at a certain length (Lo).

The catheter is provided with a number of canals running inside the catheter. Some of the canals are intended for passing stimulating means or measuring means from the proximal end of the catheter to a more distant end of the catheter, either at a position before the balloon, or at a position inside the balloon or a position after the balloon toward the distal end of the catheter.

With reference to the figures, it is important to notice that the catheter and the balloon only form part of the apparatus according to the invention, i.e. the apparatus does not consist of the catheter and the balloon, but the apparatus comprises the catheter and the balloon. Other parts of the apparatus may comprise any exterior equipment for generating the stimuli and any additional equipment for recording data, possibly provided by the gauges or other recording means attached to, connected to or in any other way assigned to the catheter and the balloon.

Example of a Possible Apparatus and Experiment

A four-electrode impedance measuring system located inside a balloon on a 120-cm-long probe was used for measurements of luminal cross-sectional area (CSA) in the duodenum. The CSA was measured according to Ohm's law from measurements of the impedance of the fluid inside the balloon. The attached balloon was 40 mm long and was made of 50-μm-thick non-conducting polyurethane. The balloon was connected via an infusion channel (2.5 mm in diameter) to a syringe that could be pushed or withdrawn to alter the balloon volume. Thus, the balloon could be inflated with an electrically conducting fluid (0.009% NaCl) to a maximum CSA of approximately 2000 mm$^2$ (diameter 50 mm) without stretching the balloon wall. The size of the balloon was chosen on the basis of pilot studies on healthy volunteer that showed the luminal CSA of duodenum at maximum applied balloon volume never exceeded 2000 mm². Thus, reliable measurements could be carried out in the physiological range without stretching the balloon wall. The probe contained three channels for pressure measurement. One side hole was located inside the balloon between the detection electrodes, while the other two side holes were located 4 cm proximal and distal to the balloon, respectively.

Healthy subjects fasted at least for 8 hours. A questionnaire was administered to all participants to assess the characteristics of visceral perception before the study started. The probe was passed into the duodenum via the nostrils after calibration of the impedance planimeter. The balloon was positioned under fluoroscopic guidance into the third portion of the duodenum. The probe was taped to the nose and adjustment of the position of the balloon was not necessary during the study. The subjects were asked to lay on the bed at the same level as the pressure transducer and to relax for 30 minutes. A meal (Nutridrink, Nutricia A/S, AllerØd, Denmark, 4 ml/kilo body weight with 6.3 Cal/ml) were given to the subjects. The meal induced a fed motility pattern in all subjects. Volume-controlled distensions were performed at various speeds and then the solution was withdrawn. The balloon was emptied for several minutes between the distensions. During this period, the subjects were asked to report any visceral perception resulting from the previous balloon distension using the questionnaire. Twenty minutes after finishing the first distension series, another similar series were done in order to evaluate the reproducibility. Twenty minutes after finishing the reproducibility test, a third distension series was done during administration of the antimuscarinic agent butylscopolamine (20 mg) in order to relax the smooth muscle. The total butylscopolamine dose (20-120 mg) was guided by the degree of abolishment of contractions and by the development of classic anticholinergic side effects.

Before the test started the subjects were trained how to use the perception questionnaire. First, they were asked to report the sensation to somatic stimuli (increasing pressure applied to the right forearm) and second, they scored symptoms during a few balloon distensions. The intensity of the non-painful sensations were scored on a 1-5 scale, where 1=vague perception of mild sensation; 2=definite perception of mild sensation; 3=vague perception of moderate sensation; 4=definite perception of moderate perception and 5=discomfort. The subjects had the possibility to score half units on the scale. A qualitative scale was added to the non-painful intensity scores, as the subjects were asked to assign the feeling at each distension steps to one of the following six sensations: fullness, colicky, warmth, stinging, pressure and others. The descriptors were chosen according to earlier studies using balloon distensions in the small intestine. The validity of the questionnaire has been demonstrated previously. For the painful sensations an electronic visual analogue scale (VAS) (Aalborg University, Aalborg, Denmark) was added anchored at 0=no pain to 5=unbearable pain. Accordingly, when the subject reported that the distension resulted in pain and/or severe discomfort (above 5 on the non-painful scale) they were asked to score the intensity of the sensation on the VAS. We selected a VAS for high intensity stimuli as we previously have demonstrated the usefulness of this instrument to assess painful visceral stimuli in the stomach, small and large intestine in healthy subjects and in patients with visceral hyperalgesia.

If the subjects reported any combination of more than two perceptions, only the strongest perception was applicable for the evaluation. In the final data analysis, the intensities of the non-painful and painful sensations were added to give a combined perception score (PS). The rationale for this addition was based on recent studies showing that, apart from being polymodal, both low—and high intensity receptors in the gut encode stimuli from the innocuous to the noxious range. This is different from the skin where non-painful and painful stimuli are mediated by specific receptor classes and where different pain qualities (such as burning and stinging pain) are transmitted by selective classes of afferents. Accordingly, the sensations encoded via individual and groups of visceral afferents probably constitute a continuing sensation from non-painful such as mild fullness/pressure to unpleasantness and pain. This corresponds with our previous experiments with electrical stimuli and pilot experiments in the current study, where increasing pressure in the duodenal balloon resulted in a smooth continuum from non-painful to painful sensations.

The CSA was estimated at steady state at each volume level. If phasic contractions were present, the mean CSA and pressure were used for further analysis. The balloon distension induced secondary peristaltic contractions consisting of pressure waves. To exclude artifacts induced by respiration, only pressure waves with amplitude greater than 7 cmH$_2$O and duration longer than 1 second were scored as contractions. The contraction frequency proximal and distal to the balloon was scored. The circumferential wall tension was calculated according to the law of Laplace for cylindrical structures as $$T=\Delta Pr$$

where T is the circumferential wall tension (kPa m), r is the balloon radius, and $\Delta P$ is the transmural pressure. Other suitable or possible ways of computing the tension and stress such as Cauchy-stress and Kirchhoff-stress may be applied under different geometric assumptions and depending on the design and function of the apparatus. The balloon pressure at a volume of 3 ml during the administration of butylscopolamine was assumed equal to the resting pressure of duodenum (i.e. the intra-abdominal pressure). Hence, the transmural pressure during distension was considered to be equal to the difference between the balloon pressure and the resting pressure. The total tension ($T_{total}$) during distension (due to both active and passive tissue properties) was determined from the distension test without the administration of butylscopolamine. The passive tension ($T_{passive}$), that only results from passive components such as the extracellular collagen was obtained from the test with butylscopolamine. The active tension ($T_{active}$) contributed by smooth muscle activity was computed using the equation:

$$T_{total}=T_{active}+T_{passive}$$

Other suitable or possible ways of computing the relationship between these tensions may be applied under different geometric assumptions and depending on the design and function of the apparatus.

The circumferential strain is the fractional change in radius computed as $$\varepsilon = \frac{r-r_0}{r_0}$$

where r is the radius at a given distension and $r_0$ is the reference radius at a wall tension of 0.002 kPa m under the assumption that the geometry was circular. At the reference tension, it was easy to determine $r_0$ graphically for the different subjects. Other suitable or possible ways of computing the strain such as Cauchy-strain and Green-strain may be applied under different geometric assumptions and depending on the design and function of the apparatus.

Stepwise inflation of the balloon resulted in a consistent mechanical response. At low volumes, the balloon distension produced numerous contractions at the distension site. The contractions faded at higher volumes (usually at more than 27 ml). Butylscopolamine clearly inhibited the contractile activity.

The CSA obtained before and during butylscopolamine administration increased as function of pressure. The latter was significant greater than the former (f=33.4, p<0.001). The volume divided by the CSA represents a measure of the axial length of the balloon when assuming a cylindrical shape. This measure increased as function of volume up to 15 ml where it approached a steady state. The curves before and during butylscopolamine administration did not differ. The bottom graph of FIG. 3 shows the total, active and passive wall tension as function of strain. Both the total and passive tension increased exponentially as function of strain. The curve representing the active tension increased slightly up to a strain of 0.3 and then decreased again. The active tension was smaller than the passive tension at strains higher than 0.36.

Figure 4:
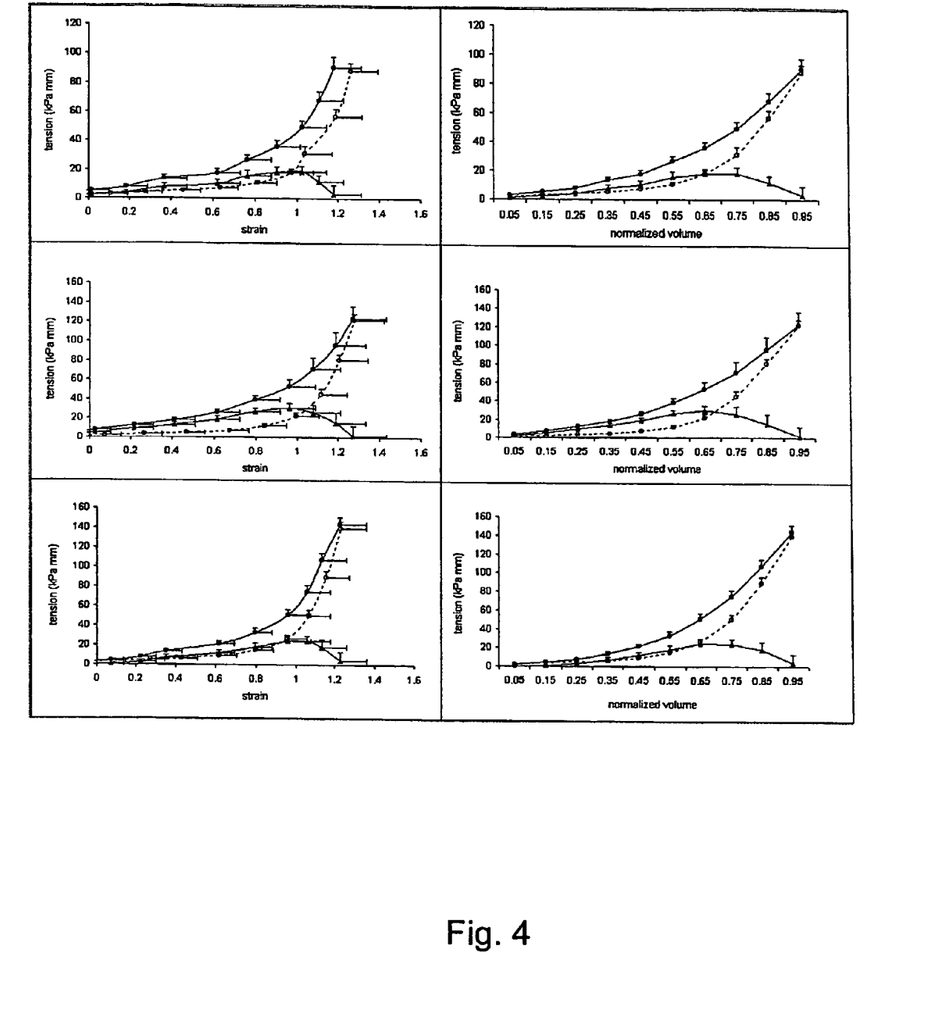
FIG. 4 shows data obtained from the human small intestine in a volunteer.

FIG. 4 illustrates the tension data as function strain and normalized volume. The total, passive and active tensions as functions of strain (left side panels) and as functions of the normalized volume (right side panels). The top, middle and bottom panels show data obtained at flow rates of 10, 25 and 50 ml per minute in the human duodenum.

Perception data. The introduction of the probe into the duodenum did not elicit significant discomfort. The balloon distensions induced the first sensation at a volume of 21±3 ml before administration of butylscopolamine. During administration of butylscopolamine the first sensation appeared at 42±1 ml. The perceptions appearing before pain showed a great individual difference. Stinging was the main perception before the pain level was reached. After the first sensation level was reached, the perception score (PS) revealed an approximate linear increase as function of volume, CSA, pressure, strain and tension. Butylscopolamine resulted in significant difference in PS as function of volume (f=8.6, p<0.005), CSA (f=35.1, p<0.001) and strain (f=6.4, p<0.01) but not pressure (f=0.01, p>0.5) and wall tension (f=0.14, p>0.5).

Secondary peristalsis. The frequency of the secondary peristalsis proximal to the balloon distension site increased as function of volume until the highest value (8.2±0.8 contractions per minute) appeared at a volume of 21 ml (FIG. 5). At higher degrees of distension the reflex activity decreased again. Distal to the balloon the frequency of contraction was 1.2±0.5 contractions per minute before administration of butylscopolamine. The drug markedly reduced the distension-evoked motility. During the administration of butylscopolamine, the highest values proximal and distal to the balloon were 2.7±1.2 and 0.2±0.2 contractions per minute. The maximum appeared at a volume of 21 ml.

To exclude time-and load-dependent biomechanical effects as well as conditioning effects, i.e. changes in sensibility in subsequent distension series, we evaluated the reproducibility by adding a second distension series before the administration of butylscopolamine. The CSA (f=0.57, p>0.4), pressure (f=1.37, p>0.2) and PS (f=0.23, p>0.5) did not differ significantly from the first to the second series (FIG. 6).

Interpretation of the above data. Impedance planimetry enabled us to characterize the luminal dimension and wall tension in the human duodenum along with the peristaltic reflex. The administration of the antimuscarinic drug butylscopolamine allowed us to investigate active and passive tissue behaviour. The duodenal CSA increased during administration of butyiscopolamine. The distension protocol can be considered isometric in the sense that the balloon volume was controlled. The length-tension test reproduces the well-known length-tension diagrams obtained in smooth muscle strips from various organs. The strips model has been used extensively in physiology and pharmacology research. The model proposed in this study has the advantage that it is performed under in vivo conditions with preserved organ geometry. The fed state was chosen because it is more stable when compared to the fasting state where variations in smooth muscle tone occur.

It is well known that the passive elastic behaviour of biological tissues is exponential. This mechanical feature protects the tissue against overdistension and damage at high luminal pressure loads while distending easily and facilitating flow in the physiological pressure range. In arteries, it has been demonstrated that collagen bears circumferential loads at high stress levels. As gastrointestinal tissue is rich in collagen, it is likely that collagen is a major determinant of the passive mechanical properties. The tension-strain curve demonstrated that the passive elastic behaviour of duodenum in vivo is exponential and hence can play a role in protecting tissue against high stress. At high loads the tissue elastic behaviour is contributed mainly by the passive tension curve, whereas at low stress levels, i.e. in the physiological range, the active tension curve dominates the tissue elastic behaviour, facilitating bolus transport. Thus, the distensibility in vivo depends not only on the passive properties but also on the physiological state of smooth muscle.

The results may shed some light on the discussion regarding the visceral sensation receptors in man. The current concept is that the mechanoreceptors are tension-sensitive receptors that lie in-series or in-parallel with the muscle cells. This concept is borrowed from striated muscle physiologists and should yet be regarded as a working hypothesis since no clear evidence support it in GI studies. It is basically a uni-axial model that does not account for more complex biomechanical properties such as the distribution of the deformation field and that different receptor populations may exist. Furthermore, there seems to be no evidence for the receptor being dependent of tension rather than strain. Nevertheless the model may serve as a basis for further development of theoretical and practical work. Using this model most data obtained from animal studies support the view that the mechanoreceptors are in-series with the muscle. The rationale is that both passive stretch and active contractions can activate the receptors. However, data obtained in animal models cannot directly be extrapolated to man, although Thewisen et al recently provided evidence that the rectal mechanoreceptor response in the non-noxious range is comparable in cats and humans. Human studies are difficult to interpret due to the central processing of pain stimuli compared to animal models with direct recording of afferent nerve activity. Taking the above limitations into account it is feasible that the PS-strain relation found in this study support the "in-series receptor theory". The argument is that the sensation score decreased after relaxation of the muscles with the same degree of fractional change in length. If the receptors were "in-parallel" the forces applied at the receptors would be unaltered despite relaxation of the myofilament, thus giving the same degree of perception. During relaxation the same tension resulted in an increase in strain due to relaxation of the smooth muscles. The same load is, however, stretching the "in-series" receptors, resulting in an unchanged PS-tension curve despite relaxation. If the receptors were "in-parallel" the relaxation would theoretically have resulted in an increased perception during simultaneous elongation of both muscle and receptor. Although disputed, different (low/high/intensity encoding) receptors may exist and the approximation between the two curves (with/without butylscopolamine) in the PS-strain plot in the nociceptive range, may suggest other receptor characteristics for the suggested high threshold receptors. The sparse data in this range, however, does not allow any firm conclusions. In contrast to the study on rectum by Thewisen et al, our curves did not saturate for the higher distension pressures. This may be related to the different parts of the GI tract studied as well as to different ways of computing wall tension. It is also worthwhile to notice that changes in balloon length (and thereby changes in the size of the stimulation field) may contribute to the shape of the perception curves and in part explain the polymodal shape.

The invention claimed is:

1. A method for investigating force-deformation properties in muscles walls of a bodily hollow system using a balloon, wherein (i) said system has an opening, (ii) said balloon is situated between a proximal end and a distal end of a catheter, (iii) said catheter comprises an inside canal, and (iv) said method comprises the steps of:
    (a) inflating said balloon until said balloon abuts the inner wall of said system, wherein the inflation is a stepwise distension or a ramp distension with controlled distension rates, such that said balloon and said catheter are fixed longitudinally in relation to said system, and subsequently
    (b) introducing a mechanical stimulus by the inflated balloon to the muscles in the walls, wherein said mechanical stimulus is introduced between the opening of said system and the distal end of the catheter through said canal,
    (c) measuring the change of a physical property of the balloon during inflation of the balloon, wherein said physical property is a dimensional state of the balloon itself, is correlated to a force induced to the balloon, or is a mutual state between the balloon and the wall of the system, whereby
        (i) data related to the total tissue properties is obtained from a distention test in the absence of an muscle relaxant, and
        (ii) data related to the passive tissue properties is obtained from a distention test in the presence of an muscle relaxant,
    (d) computing the data related to the active tissue properties from the data related to the passive tissue properties and the total tissue properties obtained from step (c) according to the equation: total tissue properties=active tissue properties+passive tissue properties, and
    (e) deriving force-deformation diagrams from the data related to the passive tissue properties and the active tissue properties.

2. The method according to 1, wherein
    (i) step (c) further comprises measuring a change of a physical state of said system during inflation of the balloon, wherein said physical state is correlated to a corresponding physical property of the balloon, or to a mutual state between the balloon and the wall of the system, and
    (ii) said force-deformation diagrams comprise length-tension diagrams, tension-strain diagrams, and stress-strain diagrams under various conditions comprising during administration of drugs in animals or persons with diseases.

3. The method according to claim 1, wherein the bodily hollow systems is selected from the group consisting of the digestive system, the urogenital tract, the cardiovascular system, the ear canal, and the posterior nares.

4. The method according to claim 1, wherein said computing data related to total force tissue properties is performed in absence of muscle stimulation by drugs.

5. The method according to claim 1, wherein said computing data related to active force tissue properties is performed based on the values measured during a balloon being introduced into a hollow system showing short-lasting muscle contractions.

6. The method according to claim 1, wherein said computing data related to active force tissue properties is performed based on the values measured during a balloon being introduced into a hollow system showing long-lasting muscle contractions.

7. The method according to claim 1, wherein said computing data related to active force tissue properties is performed based on the intermediate values computed from values measured during a balloon being introduced into a hollow system showing any type of muscle contractions.

8. The method according to claim 1, wherein the method is performed in vivo, and said opening is exteriorly accessible.

9. The method according to claim 1, wherein the method is performed in vitro.

10. The method according to claim 1, wherein:
    (i) said mechanical stimulus introduces a change in pressure inside the balloon,
    (ii) said pressure is used for computing the circumferential tension applied by the balloon to the internal surface of the wall of the system, and
    (iii) said change in pressure is measured as the magnitude of said mechanical stimulus.

11. The method according to claim 1, wherein:
    (i) said mechanical stimulus induces a change of volume of the balloon,
    (ii) said volume is used for computing the circumferential strain applied by the balloon to the internal surface of the wall of the system, and
    (iii) said change in volume is measured as the magnitude of said mechanical stimulus.

12. The method according to claim 1, wherein:
    (i) said mechanical stimulus induces a change of the diameter of the balloon,
    (ii) the diameter is used for computing of the circumferential strain applied by the balloon to the internal surface of the wall of the system, and
    (iii) said change of diameter is measured as the magnitude of said mechanical stimulus.

13. The method according to claim 1, wherein:
    (i) said mechanical stimulus introduces a change in cross-sectional area of the balloon,
    (ii) said area is used for computing of the circumferential strain applied by the balloon to the internal surface of the wall of the system, and
    (iii) said change in cross-sectional area is measured as the magnitude of said mechanical stimulus.

14. The method according to claim 1, wherein:
    (i) said mechanical stimulus introduces a change in tension of balloon,
    (ii) said tension is used for computing of the circumferential tension applied by the balloon to the internal surface of the wall of the system, and
    (iii) said change in tension is measured as the magnitude of said mechanical stimulus.

15. The method according to claim 1, wherein:
(i) said mechanical stimulus introduces a change in the dimensional state of the balloon,
(ii) said inflation induces a circumferential strain applied by the balloon to the internal surface of the wall of the system, and
(iii) said induced strain is measured as the magnitude of said mechanical stimulus.

16. The method according to claim 1, wherein the bodily hollow system is the stomach.

17. The method according to claim 1, wherein the bodily hollow system is the bladder.

18. The method according to claim 1, wherein the bodily hollow system is the heart.

19. The method according to claim 1, wherein the bodily hollow system is the eustachian canal.

20. The method according to claim 1, wherein said computing data related to passive force tissue properties is performed during muscle relaxation.

21. The method according to claim 20, wherein muscle relaxation is induced by muscle relaxing drugs.

22. The method according to claim 1, wherein said computing data related to total force tissue properties is performed during muscle stimulation.

23. The method according to claim 22, wherein muscle stimulation is induced by muscle stimulating drugs.

24. A method for investigating force-deformation properties in muscles walls of a bodily hollow system using a balloon, wherein (i) said system has an opening, (ii) said balloon is situated between a proximal end and a distal end of a catheter, (iii) said catheter comprises an inside canal, and (iv) said method comprises the steps of:
(a) inflating said balloon until said balloon abuts the inner wall of said system, wherein the inflation is a stepwise distension or a ramp distension with controlled distension rates, such that said balloon and said catheter are fixed longitudinally in relation to said system, and subsequently
(b) introducing a mechanical stimulus by the inflated balloon to the muscles in the walls, wherein said mechanical stimulus is introduced between the opening of said system and the distal end of the catheter through said canal,
(c) measuring the change of a physical state of said system during inflation of the balloon, wherein said physical state is correlated to a corresponding physical property of the balloon, or to a mutual state between the balloon and the wall of the system, whereby
   (i) data related to the total tissue properties is obtained from a distention test in the absence of an muscle relaxant, and
   (ii) data related to the passive tissue properties is obtained from a distention test in the presence of an muscle relaxant,
(d) computing data related to the active tissue properties from the data related to the passive tissue properties and the total tissue properties obtained from step (c) according to the equation: total tissue properties=active tissue properties+passive tissue properties, and
(e) deriving force-deformation diagrams from the data related to the passive tissue properties and the active tissue properties, wherein the force-deformation diagrams comprise length-tension diagrams, tension-strain diagrams, and stress-strain diagrams under various conditions comprising during administration of drugs in animals or persons with diseases.

* * * * *